(12) United States Patent
Danenberg et al.

(10) Patent No.: US 9,402,567 B2
(45) Date of Patent: Aug. 2, 2016

(54) FOOT MEASURING DEVICE

(71) Applicant: AETREX WORLDWIDE INC., Teaneck, NJ (US)

(72) Inventors: Noam Danenberg, Hod Hasharon (IL); Gerby Eliaho, Netanya (IL); Yuval Bechor, Tel Aviv (IL)

(73) Assignee: AETREX WORLDWIDE INC., Teaneck, NJ (US)

( * ) Notice: Subject to any disclaimer, the term of this patent is extended or adjusted under 35 U.S.C. 154(b) by 1 day.

(21) Appl. No.: 14/867,810

(22) Filed: Sep. 28, 2015

(65) Prior Publication Data

US 2016/0015298 A1     Jan. 21, 2016

Related U.S. Application Data

(63) Continuation-in-part of application No. 12/811,463, filed as application No. PCT/IL2009/000018 on Jan. 5, 2009, now abandoned.

(51) Int. Cl.
A61B 5/107    (2006.01)
A61B 5/103    (2006.01)

(52) U.S. Cl.
CPC .............. *A61B 5/1079* (2013.01); *A61B 5/1036* (2013.01); *A61B 5/1074* (2013.01)

(58) Field of Classification Search
CPC .................................................. A61B 5/1079
See application file for complete search history.

(56) References Cited

U.S. PATENT DOCUMENTS

| 3,689,079 | A | * | 9/1972 | Hitoshi | G11B 3/095 250/231.13 |
| 5,659,395 | A | * | 8/1997 | Brown | A43D 1/025 33/3 R |
| 2007/0253004 | A1 | * | 11/2007 | Danenberg | A43D 1/025 356/635 |
| 2010/0152619 | A1 | * | 6/2010 | Kalpaxis | A61B 5/0002 600/592 |

* cited by examiner

*Primary Examiner* — Toan Le
*Assistant Examiner* — Manuel Rivera Vargas
(74) *Attorney, Agent, or Firm* — Roach Brown McCarthy & Gruber, P.C.; Kevin D. McCarthy

(57) ABSTRACT

An apparatus for measuring the dimensions of human feet is comprised of a base and a cover, which fits over it to define the borders of two essentially rectangular wells into which the feet to be measured are placed. A pressure pad assembly comprising a matrix of sensors is placed at the bottom of base. The walls of the wells are defined by PCBS comprising arrays comprised of a multitude of emitter/detector pairs, which are used to make length and width measurements of said feet. MCUs on the pressure pad assembly and computation means comprise software algorithms that automatically make length, width, and pressure measurements and correct errors in the length and width measurements caused by misalignment of the feet in the wells. Methods of using the apparatus are also presented.

16 Claims, 6 Drawing Sheets

FOOT MEASURING DEVICE

FIELD OF THE INVENTION

The present invention is related to the field of measuring human feet for the purpose of determining shoe size and insole type. Specifically, the invention relates to an apparatus for optical measurement of feet which does not contain motors or moving parts.

BACKGROUND OF THE INVENTION

The problem of obtaining accurate foot measurements has existed since man first started to wear shoes. Many devices of varying degrees of complexity have been proposed over the years for providing two-dimensional measurements of length and width of the human foot in order to provide appropriately fitted shoes and insoles. Representative of such devices is that of Charles Brannock, disclosed in U.S. Pat. No. 1,725,334. Brannock's device, familiar to anyone who has ever visited a shoe store, basically consists of two slides mounted on an indexed base plate to determine the length and width of the foot.

Since Brannock's day the technology has improved, providing pressure sensors and light sensitive sensors of various types to measure the length and the width of the foot. In U.S. Pat. No. 5,659,395 is presented a system that improves somewhat on the existing foot measurement systems. The system disclosed in this patent utilizes a combination of a pressure pad assembly for each foot surrounded by a linear array of infrared light emitting diodes (LEDs) located around the perimeter on two sides of each pressure pad and two corresponding arrays of phototransistors acting as detectors on the opposing sides. The length and width measurements are determined by combining information provided by the pressure pad with the data from the infrared arrays indicating which of the optical paths are blocked by the foot placed between the emitters and the receivers. The apparatus in U.S. Pat. No. 5,659,395 additionally has matrices of emitters and corresponding detectors to give height information at selected locations along the perimeter of the foot. However, U.S. Pat. No. 5,659,395 possess several significant disadvantages. First, the relatively large size and complexity of the apparatus makes it an expensive device, which may be prone to malfunction. Second, the accuracy of the measurements is limited by the size of the LEDs, because if a foot ends between two emitters, the reading will determine the size according to the last optical path blocked, with no consideration of in-between cases. Additionally, in order to reduce errors due to outside light sources, the apparatus applies modulated current to the emitters and modulation filters to detect the modulated signals. This introduces a significant amount of components and complexity to the electronic circuitry.

U.S. Pat. No. 7,336,377 to the applicant of the present application describes a foot measuring device for the determination of foot dimensions. The device comprises two emitter/detector pairs and two pressure pads assemblies. The feet are measured by the use of a mechanical arrangement, which enables the emitter and detector of each pair to be moved in parallel along two pairs of rails that are oriented in mutually orthogonal directions. Finally, the data obtained is stored, analyzed and displayed.

The field of retail shoe stores is an intensely competitive one in which each store owner must be able to provide a high level of service in order to achieve and maintain his share of the market. Part of providing such service would be to make available to his customers a system, for measuring their feet and using these measurements to supply good fitting shoes. In order to be able to provide this service, the measuring apparatus must be durable, reliable, and easy to operate; must provide accurate, easy to interpret results; and must be relatively inexpensive to purchase and operate.

It is a purpose of the present invention to provide an apparatus for measuring the length and width of the human foot.

It is another purpose of the present invention to provide an apparatus for measuring the length and width of a human foot that does not contain motors and moving parts, and that is easy to operate.

It is still another purpose of the present invention to provide an apparatus for measuring the length and width of a human foot with a high degree of accuracy.

It is yet another purpose of the present invention to provide an apparatus for measuring the length and width of a human foot that is relatively inexpensive to purchase and to operate.

It is still another purpose of the present invention to provide a method for calculating the exact length and width of a human foot in case that the foot was placed improperly in the measuring apparatus.

Further purposes and advantages of this invention will appear as the description proceeds.

SUMMARY OF THE INVENTION

In a first aspect the invention is an apparatus for measuring parameters of human feet. The apparatus comprises a housing and computation means.
Wherein,
A. the housing comprises:
  a) a base, which comprises a bottom plate that rests on a floor;
  b) a cover, which fits over the base, the cover comprising two rectangular openings through its upper surface that are separated by a bridge element, which defines two essentially rectangular wells into which the left and right feet to be measured are placed respectively;
  c) tabs attached to the bottom plate and configured to secure the cover to the base;
  d) a pressure pad assembly in direct contact with the bottom plate in each of the wells, the pressure pad assembly comprising: a PCB on which is created integrated electric circuits comprising two matrices of pressure sensors, a communication microcontroller (MCU) responsible inter alia for communication with the external computing means, a LED MCU, dedicated to operating the arrays of light sources and detectors in both wells, a pressure pad MCU dedicated to measurement of output voltage from the pressure sensors, a switching multiplexer, an operational amplifier, and other circuit elements;
  e) a plurality of sources arranged in two arrays created on two PCBs that define two of the walls of each of the wells, wherein each source array comprises two rows of equally spaced light emitters arranged in two contiguous levels, wherein the light emitters in the upper level are offset from those in the lower level by one half of the width of an individual emitter;
  f) a plurality of detectors arranged in arrays created on two PCBs that define the other two walls of each of the wells, wherein each array comprises two rows of equally spaced detectors arranged in two contiguous levels, wherein the detectors in the upper level are offset from those in the lower level by one half of the width of an individual detector and wherein each array of detectors is on a wall opposite the wall on which an array of light emitters is supported;

g) electric circuits created on each of the PCBs that comprise the source and detector arrays, the electric circuits configured to supply un-modulated electric current to the light sources, to supply power to the detectors, and to transfer the output of the detectors to the LED MCU;

h) attachment means configured to structurally and electrically connect the PCBs that comprise the source and detector arrays together to define the walls of the rectangular wells;

i) static filters configured to block ambient light, one filter placed immediately in front of each detector array, the filters created from two sheets of Polaroid film that are arranged in a fixed orientation to each other with their molecules aligned at 90 degrees to each other; and B. the computation means comprises:
  a) a processor;
  b) one or more memory modules;
  c) a display device;
  d) input means;
  e) a software algorithm which places the apparatus in a polling mode in which the pressure sensors are periodically interrogated to determine if any weight has been placed upon them, whereupon, when a pressure sensor senses a force indicating that a foot has been placed in the well of the housing a signal is sent to the processor to begin executing measurement software; and
  f) a software algorithm which uses information supplied from the pressure pad MCU to correct errors in the length and width measurements caused by misplacement/misalignment of the feet in the wells;
  g) a software algorithm which uses information supplied from the LED MCU to determine the length and width of measured feet in mm, cm, or inches, wherein the LEDs MCU on the PCB of the pressure pad assembly comprises:
  a) a software algorithm which is configured to run in order to measure in numbers of blocked LEDS the length and the width of a foot placed in a well of the housing, the algorithm comprises two phases:
    i) a data collection phase comprising: activating the electric circuits for each emitter and corresponding detector array such that the light sources and their corresponding detectors are activated one pair at a time sequentially starting from one end of the array and assigning and storing in a memory module either a zero or a one to each LED in the array to indicate whether light from that LED has been detected or not; and
    ii) a data analysis phase in which the data from the first phase is analyzed by reading the assigned numbers from eight detectors at a time and allowing two of the detectors to give false readings; and
  b) a software algorithm activated on startup of the apparatus and configured to self-test each emitter/detector pair by activating the emitter/detector pairs sequentially, saving in a memory the light value measured when each LED is activated, and comparing these stored values to the light values detected for each LED during the measurement of a foot; and wherein the pressure pad MCU on the PCB of the pressure pad assembly comprises a software algorithm which is configured to measure the voltage from each of the sensors in the two matrices of pressure sensors created on the printed circuit board of the pressure pad assembly and to convert the measured voltages into pressure maps.

In embodiments of the apparatus of the invention the computation means are an integral part of the apparatus.

In embodiments of the apparatus of the invention at least a part of the computation means are provided by an external computation unit that is not an integral part of said apparatus. The external computation unit can be one of a personal computer, a laptop computer, a tablet computer, a portable communication device, and a smartphone.

In embodiments of the apparatus of the invention the parameters of the feet that are measured are at least one of length, width, metatarsal pressure, and arch depth.

In embodiments of the apparatus of the invention the pressure pad assembly comprises a less than one mm thick foil conductive mat on top of a thin PCB on which has been created an electric circuit comprising two matrices of pressure sensors, and a relatively thick PVC layer under the PCB layer.

In embodiments of the apparatus of the invention the light sources are infrared light emitting diodes (LEDs) and the detectors are infrared sensitive phototransistors.

In embodiments of the apparatus of the invention the LEDs emit light having a wavelength of 940 nm, the detectors detect light over a wide wavelength range, and the Polaroid films transmit approximately over 98% of incident light above about 900 nm and linearly polarizes incident light having wavelength of less than approximately 825 nm.

In embodiments of the apparatus of the invention the external computation means is linked to the housing by means of a communication channel. The communication channel is configured to operate according to one of the following technologies: land line, Bluetooth, WiFi, internet, or cellular.

In a second aspect the invention is a method for using the apparatus of the first aspect to measure the length and width of the feet of a human. The method comprises the following steps:
  i) providing an apparatus of the first aspect of the invention;
  ii) executing a software algorithm to self-test each emitter/detector pair before a foot is placed in a well in the housing of the housing of the apparatus and later comparing the results of the self-tests to data collected from foot measurements;
  iii) placing the feet in the wells;
  iv) initiating the measurement process;
  v) executing a measurement software algorithm which is configured to measure the length and the width of feet placed in the wells of the housing, the algorithm comprises two phases:
    a) a data collection phase comprising: activating the electric circuits for each emitter and corresponding detector array such that the light sources and their corresponding detectors are activated one pair at a time sequentially starting from one end of the array and assigning and storing in a memory module either a zero or a one to represent each LED in the array to indicate whether light from that LED has been detected or not; and
    b) a data analysis phase in which the data from the first phase is analyzed by reading the assigned numbers from eight detectors at a time and allowing two of the detectors to give false readings;
  vi) calculating the apparent length and width of the feet from the data received from the data analysis phase
  vii) sending the apparent length and width of the feet calculated at the end of the data analysis phase to the external computation means;

viii) activating the pressure sensors incorporated in the pressure pad assemblies and creating a pressure map from the pressure sensors in each well;

ix) sending the pressure map for each well to the computation means;

x) calculating the orientation of the feet from the data received from the pressure pad assemblies;

xi) in case of misplacement/misalignment of the feet in the wells of the apparatus, executing a software algorithm for correcting the calculated apparent length and width of the feet, thereby obtaining the actual length and width of the feet; and xii) displaying the results of the measurements.

In embodiments of the method of the invention steps (v) to (vii) are carried out simultaneously with steps (viii) to (xi).

In embodiments of the method of the invention the measurement process is initiated by executing a software algorithm which places the apparatus in a polling mode in which the pressure sensors are periodically interrogated to determine if any weight has been placed upon them, whereupon, when a pressure sensor senses a force indicating that a foot has been placed in the well of the housing a signal is sent to the processor to begin executing the measurement software. In these embodiments of the method of the invention after step (ii) is carried out once, steps (v) to (xii) are carried out multiple times until the apparatus is turned off. In these embodiments of the method of the invention after placing the feet in the wells to initiate the measurement process, steps (v) to (xii) are carried out automatically by the software in MCUs and the computation means.

In embodiments of the method of the invention the results displayed comprise at least one of: measurements of length, width, metatarsal pressure and arch depth of the foot expressed in centimeters or inches, a recommended shoe size, recommended orthotics, and pictures of appropriately sized shoes of different types that are either available in the inventory of the store or can be ordered for home delivery All the above and other characteristics and advantages of the invention will be further understood through the following illustrative and non-limitative description of preferred embodiments thereof, with reference to the appended drawings.

DETAILED DESCRIPTION OF PREFERRED EMBODIMENTS

Figure 1:
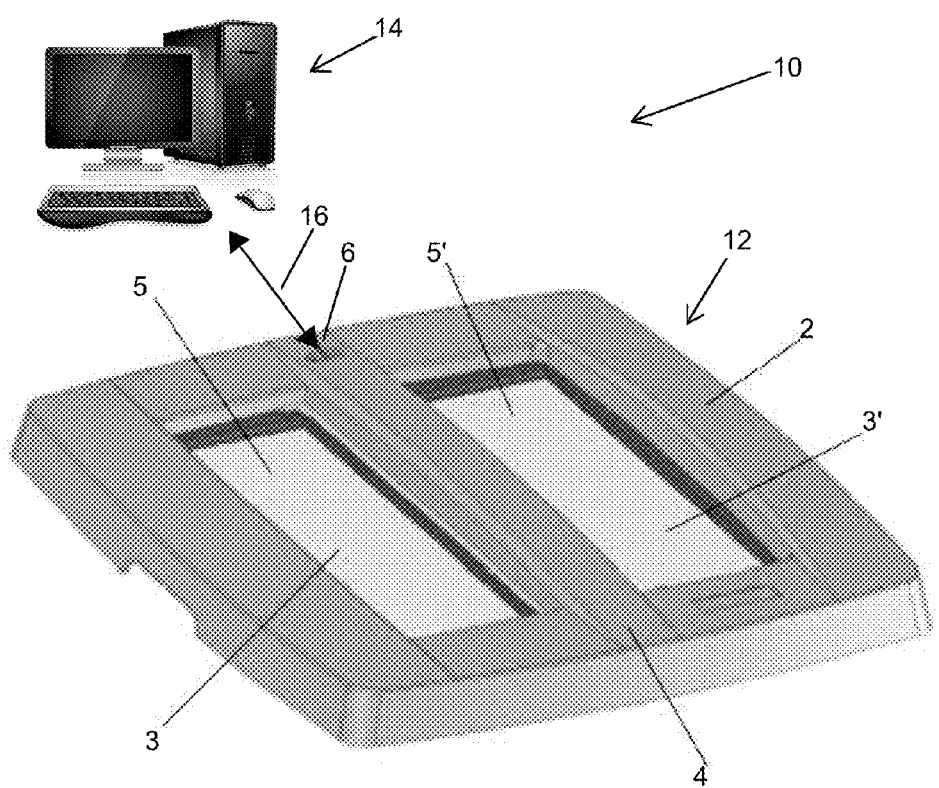
FIG. 1 is a perspective view showing the external view of an embodiment of the measuring apparatus of the invention.

The invention is an apparatus comprising pressure pads and arrays of light emitters and detectors for measuring parameters of feet such as length, width, and arch depth that are used to recommend shoes that will correctly fit the measured foot. FIG. 1 is a perspective view, which symbolically shows an external view of an embodiment of the measuring apparatus 10 of the invention. Measuring apparatus 10 is comprised of a housing 12 and external computation means 14.

It is noted that the term "computation means" is used herein to encompass not only devices that are configured to carry out mathematical processes, but is meant to represent all components of modern computer systems. External computation means 14 may be a personal computer (PC), laptop computer, tablet computer, or a portable communication device such as a smartphone. External computation means 14 comprises a processor, one or more memory modules, a display device, input means such as a real or virtual keyboard or keypad, and dedicated software for activating the emitter and detector arrays, receiving the signals from the detectors and pressure pads, and from these data, calculating the dimensions of the foot being measured, and finally displaying the results on a display screen. External computation means 14 is linked to housing 12 by means of a communication channel 16 as symbolically shown in FIG. 1. Communication channel 16 can be a land line, such as a USB cable or a wireless link such as Bluetooth, WiFi, internet, or cellular. In an embodiment of the apparatus, some or all of the operations described as being performed by external computation means 14 can be performed by computing and display means built into the housing 12 of apparatus 10 or provided as separate components, such as a freestanding display screen.

Figure 2C:
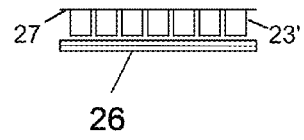
FIG. 2C is an enlarged top view of the area "C" of FIG. 2A, showing the Polarizer located in front of the detector LEDs in an embodiment of apparatus of the invention.
Figure 2B:
FIG. 2B is an enlarged view of the area "B" of FIG. 2A, showing the arrangement of the emitter/detector LEDs in an embodiment of apparatus of the invention.
Figure 2A:
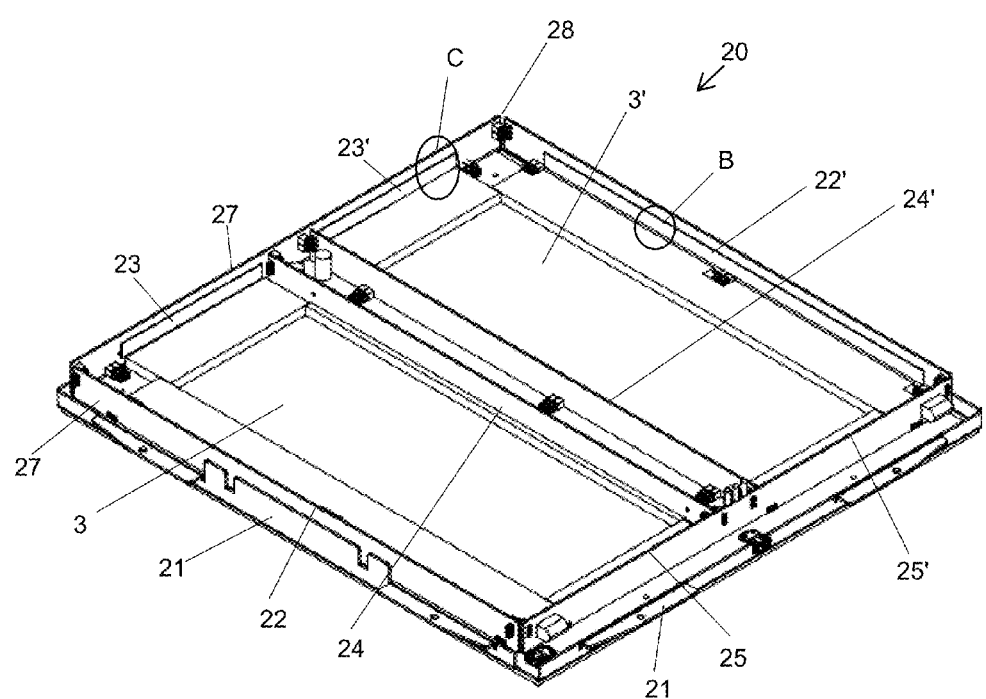
FIG. 2A is a perspective view showing the interior of an embodiment of the apparatus of the invention.

Housing 12 is comprised of a cover 2 made of a suitable material such as an impact resistant plastic or aluminum, which is fitted over a base 20 (see FIG. 2A). The cover 2 contains at least one endpoint connection 6 for Universal Serial Bus (USB) cables to enable delivery of commands from computation means 14 which controls the apparatus, as well as the transfer of the measurement readings back to the external computation means. The cover has two rectangular openings through its upper surface that are separated by a bridge element 4, which defines two essentially rectangular wells 3, 3' into which the left and right feet to be measured are placed respectively.

At the bottom of the wells 3, 3' is located a pressure pad assembly, comprising a matrix of pressure sensors 5, 5' for each well created on a single printed circuit board. In an embodiment a conductive layer, characterized by an even electrical resistance to pressure, is placed on each sensor matrix. The output of each sensor in the matrix is the resistance of the conductive layer in contact with it, wherein the measured resistance is proportional to the contact area between the conductive layer and the sensor, which in turn depends on the pressure exerted by contact of the foot on the conductive layer above the sensor. The resistance data is then translated into a pressure map. The software of the apparatus is adapted as required to include the results of the pressure measurements to give additional diagnostic information such as the structure of the arch. Additional uses of the pressure pads will be described herein below.

Figure 4:
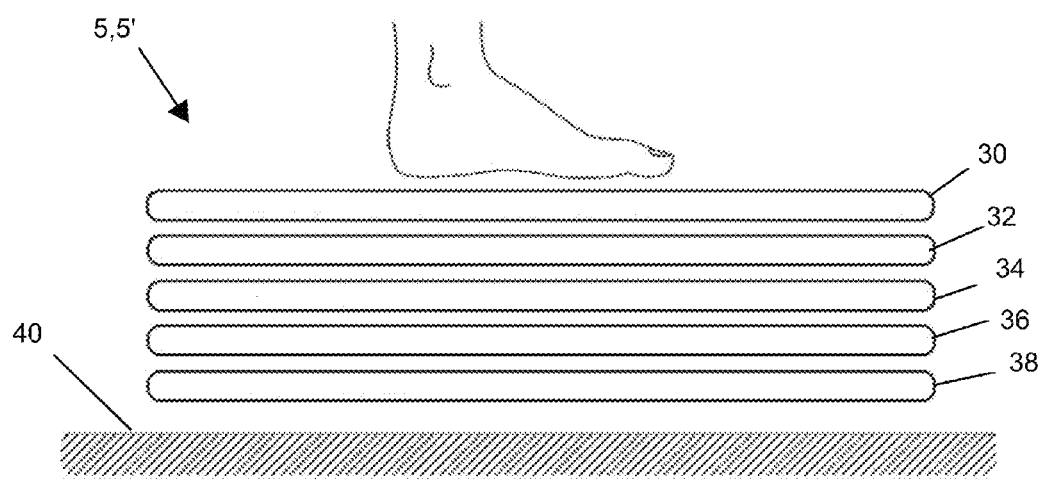
FIG. 4 schematically shows an embodiment of a layered structure at the bottom part of housing where the pressure pads are located.

FIG. 4 schematically shows a cross-sectional view of an embodiment of a pressure pad assembly comprised of a layered structure at the bottom part of housing 12 where the pressure pads 5, 5' are located. Note that in the figure a space is shown between each of the layers but in the actual structure each layer is in direct contact with the layers above and below it. The layered structure of this embodiment is comprised of the following layers:

Under the foot is a less than one mm thick foil conductive mat 30.

Beneath the foil layer is a thin PCB 32 on which has been created integrated electric circuits (ICs) comprising two matrices of pressure sensors, three microcontrollers (MCUs), a switching multiplexer, an operational amplifier, and other circuit elements. One of the MCUs, called herein the communication MCU, is responsible inter alia for communication with the external computing means; a second MCU, the LED MCU, is dedicated to operating the LEDs and detectors in both wells; and the third MCU, the pressure pad MCU, is dedicated to pressure measurements by measuring the voltage which is proportional to the contact area between the foil and the sensor for each and every sensor in both arrays. In an embodiment of the apparatus the LEDs MCU counts the length of the foot in number of LEDs, then sends the number to the Communication MCU which transfers it to the external computation means where the value of the length and the widths in millimeters is calculated. The pressure pad MCU creates the pressure map from the voltage measurements, converts it to values between 0-255 for each sensor (wherein 255 is the maximum pressure), then sends the values to the Communication MCU, which sends it to the external computation means.

PCB 32 rests on a relatively thick PVC layer 34, which in practice can be composed of two or more sheets of PVC, For example three sheets of 6 mm thick PVC giving this layer a total thickness of 18 mm.

The layer structure of the pressure pads is in direct contact with the bottom plate 36 of base 20 of the housing.

A thin piece of foam 38 is inserted between the bottom plate 36 of the housing and the floor 40 to absorb shock and even out any irregularities in the surface of the floor. It is noted that the bottom plate 36 of base 20 rests directly on and is supported over its entire area by the floor. This prevents any warping of the PCB 32 over time or flexing when a heavy person stands on the pressure pad and guarantees accurate and consistent pressure readings over time.

FIG. 2A shows the interior of the base 20 of housing 12 of an embodiment of the measuring apparatus of the invention. The base 20 is comprised of a bottom plate 36 to which are attached rectangular tabs 21. Attachment means 28 structurally and electrically connect PCBs 27 (on which the LED and detector arrays are created) together at their edges to define the walls of the wells 3, 3'. The tabs 21 are made from metal or an impact resistant plastic and are used to connect cover 2 to base 20. In an embodiment of the invention the tabs 21 are fabricated from aluminum. The base contains and supports on its surfaces and within its interior the electrical and optical components of the apparatus.

The measurement of length of a foot is carried out optically by a plurality of sources arranged as an array of equally spaced emitters created as part of an IC on a PCB forming one wall of a well and an equal number of detectors arranged in a parallel array on a PCB forming the opposite wall of each well 3, 3'. The measurement of width of the foot is carried out by similar source/detector arrays on PCBs forming the other opposite two walls of each well. On the PCBs 27 are electric circuits for each array that supply un-modulated electric current to the light sources and supply power to the detectors and transfer the output of the detectors to the LED MCU on the PCB 32 of the pressure pad assembly. Software in the LED MCU is configured to activate the light sources and their corresponding detectors one pair at a time sequentially starting from one end of the array. If a foot is placed in one or both wells 3, 3' then, when light transmitted from an emitter hits the first edge of the measured foot, the corresponding detector will not detect the light and will not send a signal to the processing unit. Once the foot no longer blocks the beams, the signal will resume again, and subsequently the software of the LEDs MCU counts the number of blocked lights and sends this number via the communication MCU to the software in the external computation means that calculates the dimensions of the measured foot in mm, cm, or inches. The feet can be measured one after the other or in another embodiment simultaneously.

In an embodiment of the apparatus of the invention the light sources are infrared light emitting diodes (LEDs) and the detectors are infrared sensitive phototransistors. The measurement is performed by the emission of a light beam by each individual emitter LED on one wall of the well and its detection (or not) by a corresponding detector on the opposite wall of the well.

FIG. 2B presents an enlarged view of the area designated as area "B" in FIG. 2A, showing the arrangement of the emitters/detectors on the PCBs 27 surrounding the wells 3, 3' in the base of the housing of the apparatus of the present invention. An increased accuracy of the measurement is achieved in the apparatus of the present invention by providing two levels of emitters and two levels of corresponding detectors, wherein the levels are contiguous to each other and the upper level is offset by one half of the width of an individual emitter/detector.

In an embodiment the light beams transmitted by the emitter LEDs are infrared rays having a wavelength of 940 nm, and the detectors detect light over a wide wavelength range. This causes a technical problem of how to separate signals from the detectors caused by the ambient light, which is mainly in the visible light range, from the signals produced by the LED's. The solution to this problem provided in the present invention is to place a static wavelength filter immediately in front of the detectors in order to prevent the ambient light from reaching the detectors. The filter is created from two sheets of Polaroid film that are arranged in a fixed orientation to each other with their molecules aligned at 90 degrees to each other. In an embodiment the Polaroid films have the following characteristics:

i. The film transmits approximately 0% of the incident light at about 350 nm, approximately 40% at 700 nm, and over 98% above about 900 nm.

ii. For wavelengths of less than approximately 825 nm the molecular structure of the film transmits only the components of the electromagnetic field having a particular orientation and absorbs all of the remaining components of the electric field of the incident light. The result is that the light transmitted through the film has only field components in one direction, i.e. the light is linearly polarized.

Thus, when two of these Polaroid sheets are oriented at ninety degrees to each other, no components of the light that has passed through the first film having wavelengths shorter than 825 nm are incident upon the second film with an orientation that allows them to be transmitted by the second film. The result of this arrangement is that all wavelengths of light shorter than 825 nm (i.e. visible light) are blocked by the films and all wavelengths longer than this wavelength (specifically about 940 nm, which is the wavelength emitted by the LEDs) are able to pass through the films with minimum attenuation. FIG. 2C presents an enlarged top view of the area designated as area "C" in FIG. 2A, showing the two layers of Polaroid film 26 in front of the array of detectors 23', which are attached to PCB 27.

An alternative method of solving the problem of the ambient light is to electronically distinguish between the light emitted by the LEDs and the ambient light by modulating the electrical current supplied to the LEDs and supplying a detection circuit that only accepts the modulated signals. The inventors of the present invention have rejected this approach because of the additional cost and complexity of the circuitry required to create and detect the modulated signals.

There are several possible activation schemes that can be carried out using the arrangement of LEDs and detectors described herein above. In one scheme the software is programmed to activate the LEDs one at a time in sequence, to ensure that each single detector receives only the signal of its corresponding emitter LED. The measurements can be carried out in any order with no effect on the results. In one example the emitter LEDs 24', which measure the length of the right foot are activated first, one after the other; then emitter LEDs 24 which measure the length of the left foot; followed by emitter LEDs 25', which measure the width of the right foot; and finally, the width of the left foot is measured by emitter LEDs 25. During a given measurement each LED is activated only once and a complete scan of a foot including the transmission of the measurements to the processing unit in computation means 14 is a very quick process that ends in about 3000 milliseconds.

As the scan proceeds the output signals from the detectors are transferred to the LED MCU. Initially, there is no obstacle between the emitter LED and the corresponding detector until the edge of the heel (toe) is reached when no signal from the detector is received indicating that the beam has been blocked. The LEDs continue to be activated and the lack of signal from the detectors continues to show that the beam is blocked until the edge of the toe (heel) is reached at which point signals from the detectors are again received by the LED MCU. The same approach is used for the measurement of the width of the feet. The number of LEDs between the disappearance and the reappearance of the signals from the detectors is stored and used to determine the required foot dimensions and shoe size of each foot.

In another embodiment the measurement process is divided into two phases. The first phase is collecting data by scanning the LEDs sequentially as described herein above and the second phase is to analyze the data received from the detectors. In the first phase a software algorithm in the LED MCU on the PCB in the pressure pad array assigns and stores in a memory module either a zero or a one to each LED in the array to indicate whether light from that LED has been detected or not. In the second phase another software algorithm runs automatically during the foot measurement for the detection of continuous values, so that if there is any inconsistency in the reading of a single LED, the software is programmed to ignore it. In this phase the data from the first phase is analyzed by reading the assigned numbers from eight detectors at a time and allowing two of the detectors to give false readings in case some of the emitters or detectors are not working properly.

Figure 5:
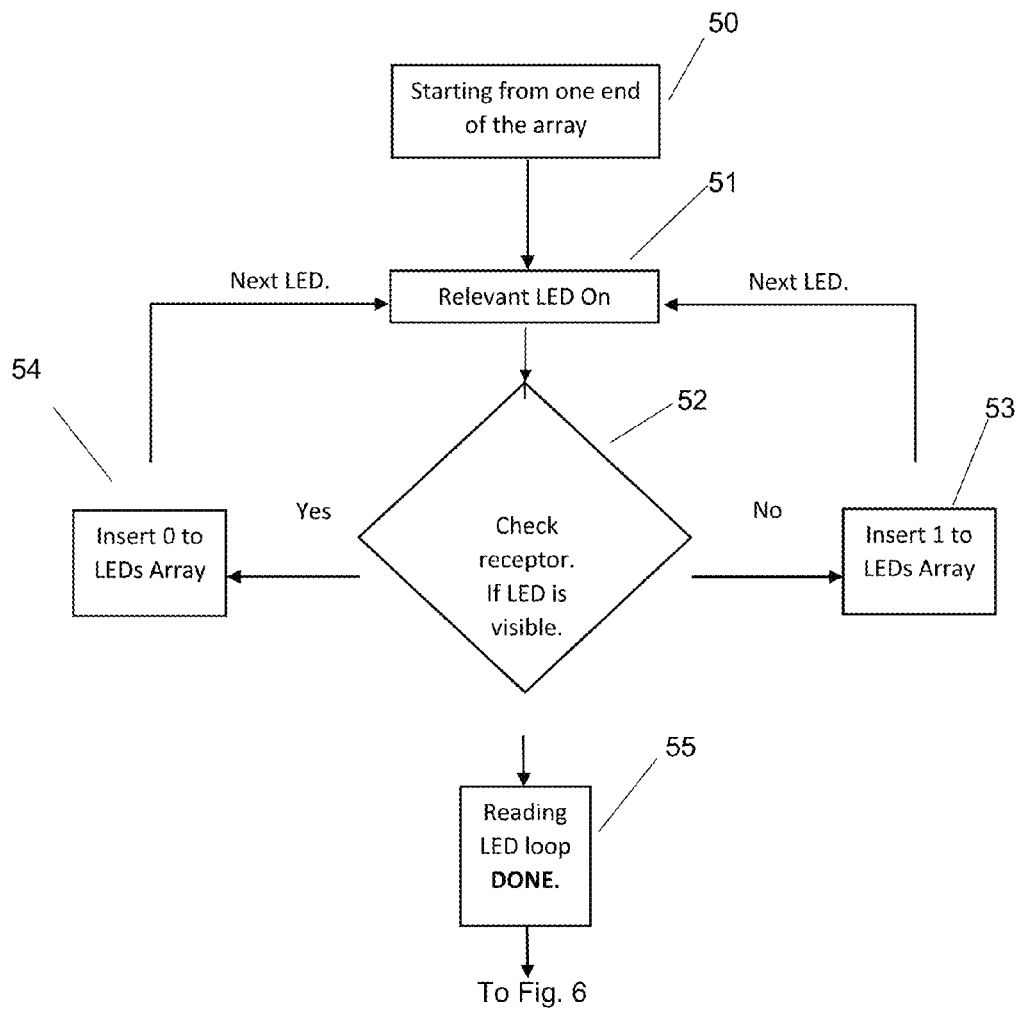
FIG. 5 and FIG. 6 are flow charts showing the steps of the process for measuring the length of one foot according to an embodiment of the invention.

FIG. 5 is a flow chart showing the steps in the first (data collection) phase of the process for measuring the length of one foot.

Figure 6:
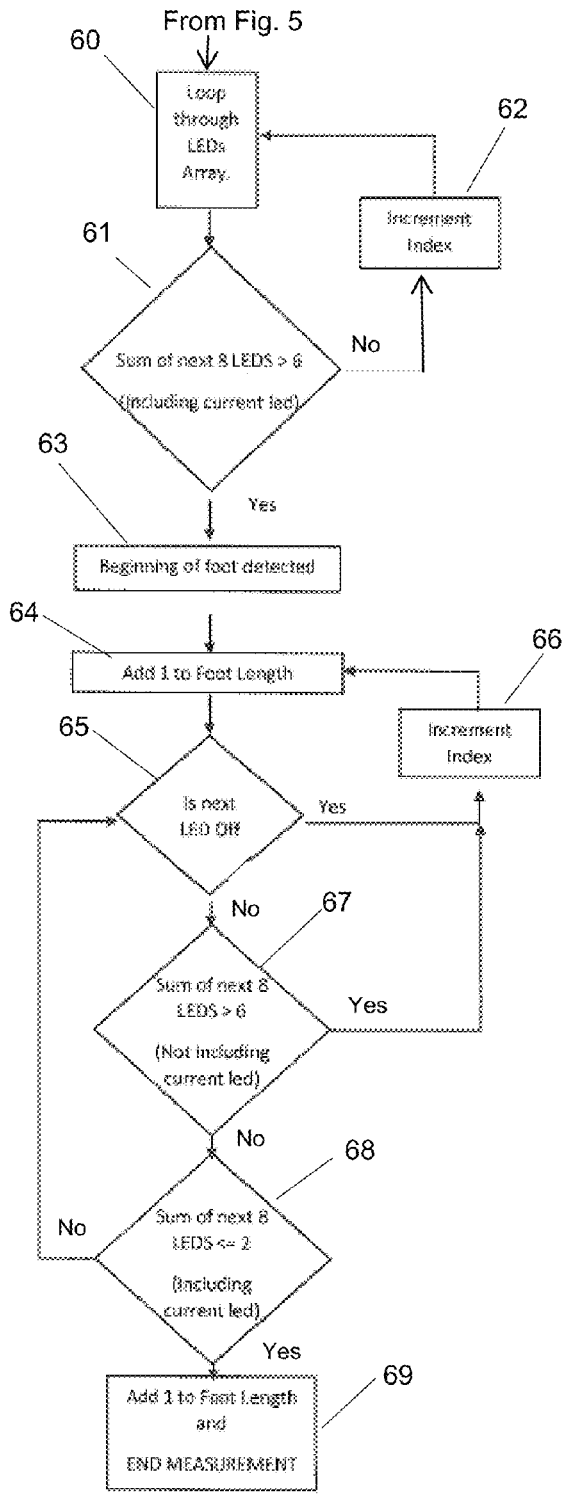

FIG. 6 is a flow chart showing the steps in the second (data analysis) phase of the process for measuring the length of one foot.

Figure 3A:
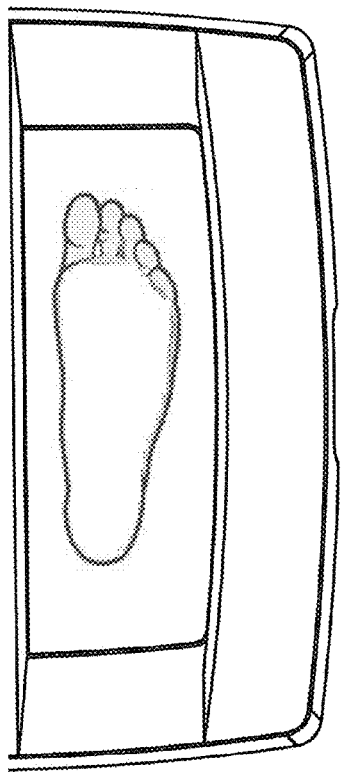
FIG. 3A is an overall view showing the outline of a foot correctly positioned in an embodiment of the measuring apparatus of the invention.
Figure 3B:
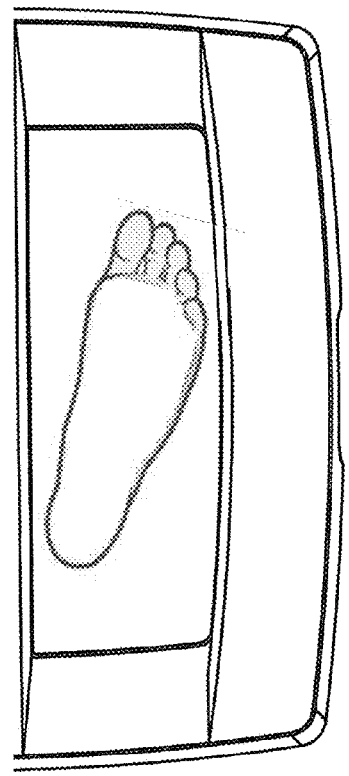
FIG. 3B is an overall view showing the outline of a foot misplaced in an embodiment of the measuring apparatus of the invention.

An embodiment of the present invention comprises a software algorithm that uses data received from the pressure pads to correct measurement errors caused by misplacing/misaligning the foot in the apparatus. FIG. 3A is an overall view showing the outline of a foot correctly positioned in the apparatus of the invention. In order to receive exact dimensions of the measured foot, it is important the foot is placed in parallel to an emitter/detector array. However, if a foot is misplaced, as shown in FIG. 3B, which is an overall view showing the outline of such foot placement, than the measurement results are used by the correction algorithm to calculate the correct length and width of the foot. To determine the correction, the algorithm uses readings from the sensors in the pressure pads to find the middle point of the top part of the foot and the middle point of the bottom part of the foot. Next, the angle between these points is determined, and finally the correct length and width are calculated based on this angle. This key functionality of the invention enables rapid measurement of the feet of any person, including children, since it does not require a certain foot position for obtaining exact and reliable results.

In order to reduce measurement errors to a minimum, upon startup the apparatus of the present invention is programmed to self-test each emitter/detector pair before the measured foot is placed in the device by sequentially activating each of the LEDs when no foot is placed in the wells and saving the output of each of the respective detectors in a memory. The output of the detectors in the self-test also includes the value for the ambient light. In the first phase of the foot measurement process the software can use these stored values to neutralize any inaccuracy in the readings resulting from degradation of the LEDs and also to neutralize any component of ambient light that is not blocked by the Polaroid filter.

For purposes of fitting a pair of shoes, the person whose feet are to be measured simply removes his/her shoes and (optionally) stockings and steps into wells 3, 3'. Optimally, the feet are placed exactly in parallel to the array of LEDs that measures the length of each foot, but this is not essential, as described above. In one mode of operation a start switch is now pressed initiating the self-testing process followed by the measurement process. However in another mode of operation the apparatus has been previously activated and the self-testing process carried out. The computation means then enters a polling mode during which the pressure sensors are periodically interrogated to determine if any weight has been placed upon them. As soon as the pressure sensors sense a force indicating that a foot has been placed in the well of the housing then a signal is sent to the MCUs on the pressure pad assembly PCB to begin executing the measurement software.

In both modes of operation all of the measuring process until the final results are displayed is carried out automatically under control of the computation means and MCUs. The MCUs process the output of the detectors and pressure sensors and transmit the measurement results to computation means 14, which either uses them immediately or stores them for later use when required.

The results of the measurements appear on the display and can appear in many forms including, but not limited to: the measurements of length, width, arch depth, and metatarsal pressure of the foot expressed in millimeters, centimeters, or inches, the recommended shoe size, recommended orthotics, and additional information such as pictures of appropriately sized shoes of different types that are either available in the inventory of the store or can be ordered for home delivery.

Although embodiments of the invention have been described by way of illustration, it will be understood that the invention may be carried out with many variations, modifications, and adaptations, without departing from its spirit or exceeding the scope of the claims.

The invention claimed is:

1. An apparatus for measuring parameters of human feet, comprising a housing and computation means; wherein
   A. the housing comprises:
      a) a base, which comprises a bottom plate that rests on a floor;
      b) a cover, which fits over the base, the cover comprising two rectangular openings through its upper surface that are separated by a bridge element, which defines two essentially rectangular wells into which the left and right feet to be measured are placed respectively;
      c) tabs attached to the bottom plate and configured to secure the cover to the base;
      d) a pressure pad assembly in direct contact with the bottom plate in each of the wells, the pressure pad assembly comprising: a printed circuit board (PCB) on which is created integrated electric circuits comprising two matrices of pressure sensors, a communication microcontroller (MCU) responsible inter alia for communication with an external computing means, a LED MCU, dedicated to operating arrays of light sources and detectors in both wells, a pressure pad MCU dedicated to measurement of output voltage from the pressure sensors, a switching multiplexer, and an operational amplifier;
      e) a plurality of sources arranged in two arrays created on two PCBs that define two of the walls of each of the wells, wherein each source array comprises two rows of equally spaced light emitters arranged in two contiguous levels, wherein the light emitters in the upper level are offset from those in the lower level by one half of the width of an individual emitter;
      f) a plurality of detectors arranged in arrays created on two PCBs that define the other two walls of each of the wells, wherein each array comprises two rows of equally spaced detectors arranged in two contiguous levels, wherein the detectors in the upper level are offset from those in the lower level by one half of the width of an individual detector and wherein each array of detectors is on a wall opposite the wall on which an array of light emitters is supported;
      g) electric circuits created on each of the PCBs that comprise the source and detector arrays, the electric circuits configured to supply un-modulated electric current to the light sources, to supply power to the detectors, and to transfer the output of the detectors to the LED MCU;
      h) attachment means configured to structurally and electrically connect the PCBs that comprise the source and detector arrays together to define the walls of the rectangular wells;
      i) static filters configured to block ambient light placed immediately in front of each detector array, the filters created from two sheets of Polaroid film that are arranged in a fixed orientation to each other with their molecules aligned at 90 degrees to each other; and
   B. the computation means comprises:
      a) a processor;
      b) one or more memory modules;
      c) a display device;
      d) input means;
      e) a software algorithm which places the apparatus in a polling mode in which the pressure sensors are periodically interrogated to determine if any weight has been placed upon them, whereupon, when a pressure sensor senses a force indicating that a foot has been placed in the well of the housing a signal is sent to the processor to begin executing measurement software; and
      f) a software algorithm which uses information supplied from the pressure pad MCU to correct errors in the length and width measurements caused by misplacement/misalignment of the feet in the wells;
      g) a software algorithm which uses information supplied from the LEDs MCU to determine the length and width of the foot in mm, cm, or inches;
   wherein the LEDs MCU comprises:
      a) a software algorithm which is configured to run in order to measure in numbers of blocked LEDs the length and the width of a foot placed in a well of the housing, the algorithm comprises two phases:
         i) a data collection phase comprising: activating the electric circuits for each emitter and corresponding detector array such that the light sources and their corresponding detectors are activated one pair at a time sequentially starting from one end of the array and assigning and storing in a memory module either a zero or a one to each LED in the array to indicate whether light from that LED has been detected or not; and
         ii) a data analysis phase in which the data from the first phase is analyzed by reading the assigned numbers from eight detectors at a time wherein up to two of the eight detectors can generate false readings; and
      b) a software algorithm activated on startup of the apparatus and configured to self-test each emitter/detector pair by activating the emitter/detector pairs sequentially, saving the light value measured when each LED is on a memory, and comparing these stored values to the light values detected for each LED during the measurement of a foot; and
   wherein the pressure pad MCU comprises a software algorithm which is configured to measure the voltage from each of the sensors in the two matrices of pressure sensors created on the printed circuit board of the pressure pad assembly and to convert the measured voltages into pressure maps.

2. A method for using the apparatus of claim 1 to measure the length and width of the feet of a human, the method comprising the following steps:
   i) providing an apparatus as defined in claim 1;
   ii) executing a software algorithm to self-test each emitter/detector pair before a foot is placed in a well in the housing of the housing of the apparatus and later comparing the results of the self-tests to data collected from foot measurements;
   iii) placing the feet in the wells;
   iv) initiating the measurement process;
   v) executing a measurement software algorithm which is configured to measure the length and the width of feet placed in the wells of the housing, the algorithm comprises two phases:
      a) a data collection phase comprising: activating the electric circuits for each emitter and corresponding detector array such that the light sources and their corresponding detectors are activated one pair at a time sequentially starting from one end of the array and assigning and storing in a memory module either a zero or a one to represent each LED in the array to indicate whether light from that LED has been detected or not; and b) a data analysis phase in which the data from the first phase is analyzed by reading the assigned numbers from eight detectors at a time wherein up to two of the eight detectors can generate false readings;

vi) calculating the apparent length and width of the feet from the data received from the data analysis phase vii) sending the apparent length and width of the feet calculated at the end of the data analysis phase to the external computation means;

viii) activating the pressure sensors incorporated in the pressure pad assemblies and creating a pressure map from the pressure sensors in each well;

ix) sending the pressure map for each well to the computation means;

x) calculating the orientation of the feet from the data received from the pressure pad assemblies;

xi) in case of misplacement/misalignment of the feet in the wells of the apparatus, executing a software algorithm for correcting the calculated apparent length and width of the feet, thereby obtaining the actual length and width of the feet; and xii) displaying the results of the measurements.

3. A method according to claim 2, wherein steps (v) to (vii) are carried out simultaneously with steps (viii) to (xi).

4. A method according to claim 2, wherein the measurement process is initiated by executing a software algorithm which places the apparatus in a polling mode in which the pressure sensors are periodically interrogated to determine if any weight has been placed upon them, whereupon, when a pressure sensor senses a force indicating that a foot has been placed in the well of the housing a signal is sent to the processor to begin executing the measurement software.

5. A method according to claim 4, wherein, after step (ii) is carried out once, steps (v) to (xii) are carried out multiple times until the apparatus is turned off.

6. A method according to claim 4, wherein after placing the feet in the wells to initiate the measurement process, steps (v) to (xii) are carried out automatically by the software in MCUs and the computation means.

7. A method according to claim 2, wherein the results displayed comprise at least one of: measurements of length, width, metatarsal pressure and arch depth of the foot expressed in centimeters or inches, a recommended shoe size, recommended orthotics, and pictures of appropriately sized shoes of different types that are either available in the inventory of the store or can be ordered for home delivery.

8. An apparatus according to claim 1, wherein at least a part of the computation means are provided by an external computation unit that is not an integral part of said apparatus.

9. An apparatus according to claim 8, wherein the external computation unit is one of a personal computer, a laptop computer, a tablet computer, a portable communication device, and a smartphone.

10. An apparatus according to claim 8, wherein the external computation unit is linked to the housing by means of a communication channel.

11. An apparatus according to claim 10, wherein the communication channel operates according to one of the following technologies: land line, Bluetooth, WiFi, internet, or cellular.

12. An apparatus according to claim 1, wherein the light sources are infrared light emitting diodes (LEDs) and the detectors are infrared sensitive phototransistors.

13. An apparatus according to claim 12, wherein LEDs emit light having a wavelength of 940 nm, the detectors detect light over a wide wavelength range, and the Polaroid films transmit approximately over 98% of incident light above about 900 nm and linearly polarizes incident light having wavelength of less than approximately 825 nm.

14. An apparatus according to claim 1, wherein the computation means are an integral part of the apparatus.

15. An apparatus according to claim 1, wherein the parameters of the feet that are measured are at least one of length, width, metatarsal pressure, and arch depth.

16. An apparatus according to claim 1, wherein the pressure pad assembly comprises a less than one mm thick foil conductive mat on top of a thin PCB on which has been created an electric circuit comprising two matrices of pressure sensors, and a relatively thick PVC layer under the PCB layer.

* * * * *